US012755378B2

(12) United States Patent
Go

(10) Patent No.: US 12,755,378 B2
(45) Date of Patent: Oct. 6, 2026

(54) DATA PROCESSING METHOD FOR DENTAL PROSTHESIS DESIGN USING PRE-PROCEDURE AND POST-PROCEDURE SCAN DATA

(71) Applicant: MEDIT CORP., Seoul (KR)

(72) Inventor: Ki Nam Go, Seoul (KR)

(73) Assignee: MEDIT CORP., Seoul (KR)

( * ) Notice: Subject to any disclaimer, the term of this patent is extended or adjusted under 35 U.S.C. 154(b) by 373 days.

(21) Appl. No.: 18/368,579

(22) Filed: Sep. 15, 2023

(65) Prior Publication Data

US 2024/0005499 A1 Jan. 4, 2024

Related U.S. Application Data

(63) Continuation of application No. PCT/KR2022/003686, filed on Mar. 16, 2022.

(30) Foreign Application Priority Data

Mar. 16, 2021 (KR) ........................ 10-2021-0034191
Mar. 16, 2022 (KR) ........................ 10-2022-0032740

(51) Int. Cl.
*G06T 7/00* (2017.01)
*A61C 13/00* (2006.01)
*A61C 19/05* (2006.01)
*G16H 30/20* (2018.01)

(52) U.S. Cl.
CPC ........ *G06T 7/0012* (2013.01); *A61C 13/0004* (2013.01); *A61C 19/05* (2013.01); *G16H 30/20* (2018.01); *G06T 2207/30036* (2013.01)

(58) Field of Classification Search
None
See application file for complete search history.

(56) References Cited

U.S. PATENT DOCUMENTS

2016/0008116 A1* 1/2016 Glinec .................... G06T 19/20 433/29
2020/0085547 A1 3/2020 Huang et al.

FOREIGN PATENT DOCUMENTS

| | | | | | |
|---|---|---|---|---|---|
| CN | 107510511 | A | | 12/2017 | |
| CN | 108720955 | A | * | 11/2018 | ............. A61C 7/002 |
| CN | 112184910 | A | * | 1/2021 | ......... G06F 18/2135 |
| EP | 3473207 | A1 | * | 4/2019 | ......... A61C 13/0004 |
| KR | 10-2015-0128713 | A | | 11/2015 | |
| KR | 10-1854729 | B | | 5/2018 | |
| KR | 10-2018-0090308 | A | | 8/2018 | |
| KR | 10-2020-0115356 | A | | 10/2020 | |
| KR | 10-2021-0013925 | A | | 2/2021 | |

(Continued)

OTHER PUBLICATIONS

English translation of CN-108720955-A. (Year: 2018).*

(Continued)

*Primary Examiner* — Thomas D Lee

(57) ABSTRACT

The data processing method according to the present disclosure includes obtaining scan data including at least one set of upper and lower jaw data and a plurality of sets of occlusion data by scanning an object, obtaining a plurality of sets of alignment scan data by aligning the upper and lower jaw data to each of different sets of occlusion data among the plurality of sets of occlusion data, and comparing the plurality of sets of alignment scan data.

9 Claims, 18 Drawing Sheets

(56) References Cited

FOREIGN PATENT DOCUMENTS

| | | |
|---|---|---|
| KR | 10-2214615 B | 2/2021 |

OTHER PUBLICATIONS

English translation of CN-112184910-A. (Year: 2021).*
International Search Report mailed Jun. 20, 2022 for International Application No. PCT/KR2022/003686 and its English translation.
European Search Report mailed on Jan. 24, 2025 from European Patent Office for Application No. 22771764.2.
Non-final Office Action mailed Dec. 22, 2023 from the Korean Patent Office for Korean Application No. 10-2022-0032740.

* cited by examiner (a)

FIG. 12

| | POST-MEDICAL PROCEDURE UPPER AND LOWER JAW DATA | PRE-MEDICAL PROCEDURE UPPER AND LOWER JAW DATA |
|---|---|---|
| FIRST OCCLUSION DATA | FIRST ALIGNMENT SCAN DATA | THIRD ALIGNMENT SCAN DATA |
| SECOND OCCLUSION DATA | SECOND ALIGNMENT SCAN DATA | FOURTH ALIGNMENT SCAN DATA |

DATA PROCESSING METHOD FOR DENTAL PROSTHESIS DESIGN USING PRE-PROCEDURE AND POST-PROCEDURE SCAN DATA

CROSS-REFERENCE TO RELATED APPLICATIONS

This application is a continuation application of International Application No. PCT/KR2022/003686, filed on Mar. 16, 2022, which claims the benefit of Korean Patent Application Nos. 10-2021-0034191, filed on Mar. 16, 2021; and 10-2022-0032740, filed Mar. 16, 2022, in the Korean Intellectual Property Office, the disclosures of which are incorporated herein in their entirety by reference.

TECHNICAL FIELD

The present disclosure relates to a data processing method.

BACKGROUND ART 3D scanning and modeling technologies are frequently used in CAD/CAM and reverse engineering fields. Particularly, in the recent dental industry, there is an increasing trend of using 3D scanners for obtaining a 3D model representing the oral cavity of a patient in order to design and provide a dental prosthesis conforming to the patient's oral cavity structure.

In general, oral cavity data to be obtained to design a dental prosthesis basically includes upper jaw data representing the patient's upper jaw structure, lower jaw data representing the patient's lower jaw structure, and occlusion data representing the occlusion structure of the patient's upper and lower jaws.

Meanwhile, when tooth information necessary for designing a dental prosthesis is obtained, a medical procedure may be performed on some of the teeth, and the occlusion data may be obtained based on data obtained by scanning the oral cavity of the patient after the medical procedure. In this case, there is a possibility of obtaining inaccurate dental prosthesis design data.

Therefore, there is a need for a method with which a user (one who performs treatment) can provide optimal treatment to a patient by obtaining more accurate data and displaying a coupling relationship between various sets of data by use of a predetermined parameter.

DISCLOSURE

Technical Problem

In order to address the aforementioned drawbacks, the present disclosure provides a data processing method for providing optimal treatment to a patient by obtaining a plurality of sets of alignment scan data from obtained scan data and by comparing the plurality of sets of alignment scan data.

The technical drawbacks which this disclosure addresses are not limited to the aforementioned ones, but unmentioned other technical drawbacks will become apparent to those skilled in the art from the description below.

Technical Solution

In order to achieve the above-described objects, the data processing method according to the present disclosure includes obtaining scan data including at least one set of upper and lower jaw data and a plurality of sets of occlusion data by scanning an object, obtaining a plurality of sets of alignment scan data by aligning the upper and lower jaw data to each of different sets of occlusion data among the plurality of sets of occlusion data, and comparing the plurality of sets of alignment scan data.

The data processing method according to the present disclosure may further include various additional components in addition to the above-described components.

Advantageous Effects

According to the above-described means for addressing the aforementioned drawbacks and the specific details to be described later, using the data processing method according to the present disclosure provides an advantage of being able to allow the user to provide to the patient an optimal dental prosthesis reflecting the general consideration of combinations among the pre-medical procedure upper and lower jaw data, the post-medical procedure upper and lower jaw data, the pre-medical procedure occlusion data, and the post-medical procedure occlusion data.

DESCRIPTION OF DRAWINGS

FIG. 12 is for explaining alignment scan data which may be generated by the combination of the occlusion data and the upper and lower jaw data.

EXPLANATION OF SYMBOLS

Figure 1:
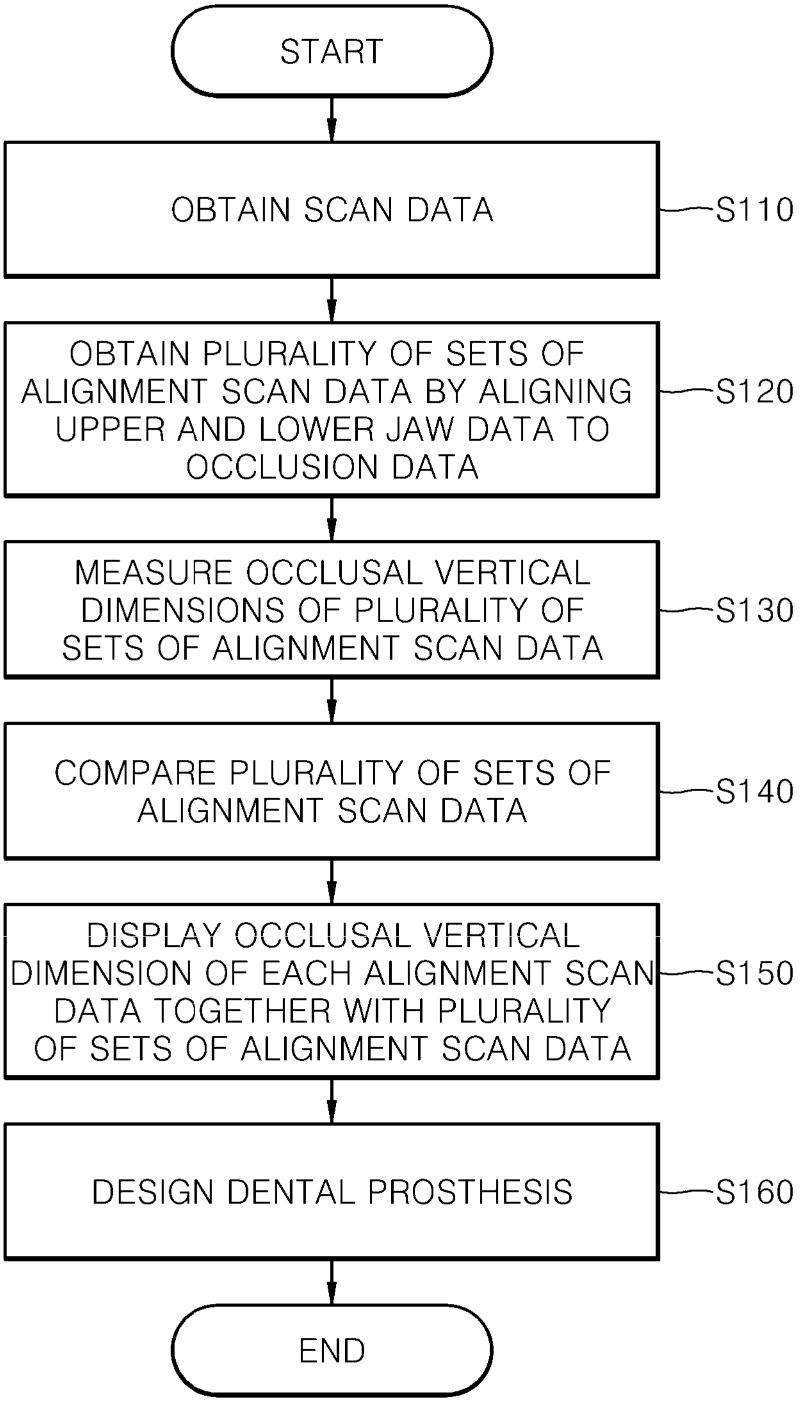
FIG. 1 shows a flowchart of a data processing method according to the present disclosure.

200: Upper and lower jaw data
210: Upper jaw data
220: Lower jaw data
221: Post-medical procedure lower jaw data

2211: Medical procedure tooth data
500: User interface

MODE FOR INVENTION

Hereinafter, some embodiments of the present disclosure will be described in detail through exemplary drawings. In adding reference numerals to components of each drawing, it should be noted that the same components have the same reference numerals as much as possible even if they are shown on different drawings. In addition, in describing an embodiment of the present disclosure, if it is determined that a detailed description of a related known configuration or function may prevent the understanding of the present disclosure, the detailed description thereof will be omitted.

In describing the components of an embodiment of the present disclosure, terms such as first, second, A, B, (a), (b), and the like may be used. These terms are only used to distinguish the component from other components, and the nature, sequence, or order of the corresponding component is not limited by the term. Further, unless otherwise defined, all terms used herein, including technical or scientific terms, have the same meaning as commonly understood by a person of ordinary skill in the art to which the present disclosure pertains. Terms, such as those defined in a commonly used dictionary, should be interpreted as having a meaning that is consistent with the meaning in the context of the related technology, and will not be interpreted in an idealized or excessively formal sense unless expressly so defined in this application.

Throughout the specification describing the present disclosure, the phrase 'upper and lower jaw data' should be interpreted as including upper jaw data and lower jaw data.

Further, the phrase 'upper and lower jaw data' may generally include at least one of data obtained by scanning an object before a medical procedure and data obtained by scanning an object after a medical procedure, and the post-medical procedure upper and lower jaw data to be described later should also be interpreted as a kind of upper and lower jaw data.

FIG. 1 shows a flowchart of a data processing method according to the present disclosure.

Referring to FIG. 1, the data processing method according to the present disclosure includes obtaining scan data (S110), obtaining a plurality of sets of alignment scan data (S120), measuring occlusal vertical dimensions of the plurality of sets of alignment scan data (S130), comparing the plurality of sets of alignment scan data (S140), displaying (S150), and designing a dental prosthesis (S160). Performing the series of steps as described above presents an advantage in that the user can provide a dental prosthesis corresponding to the oral cavity structure of the patient. Meanwhile, detailed contents of each step of the data processing method according to the present disclosure will be described later.

Figure 2:
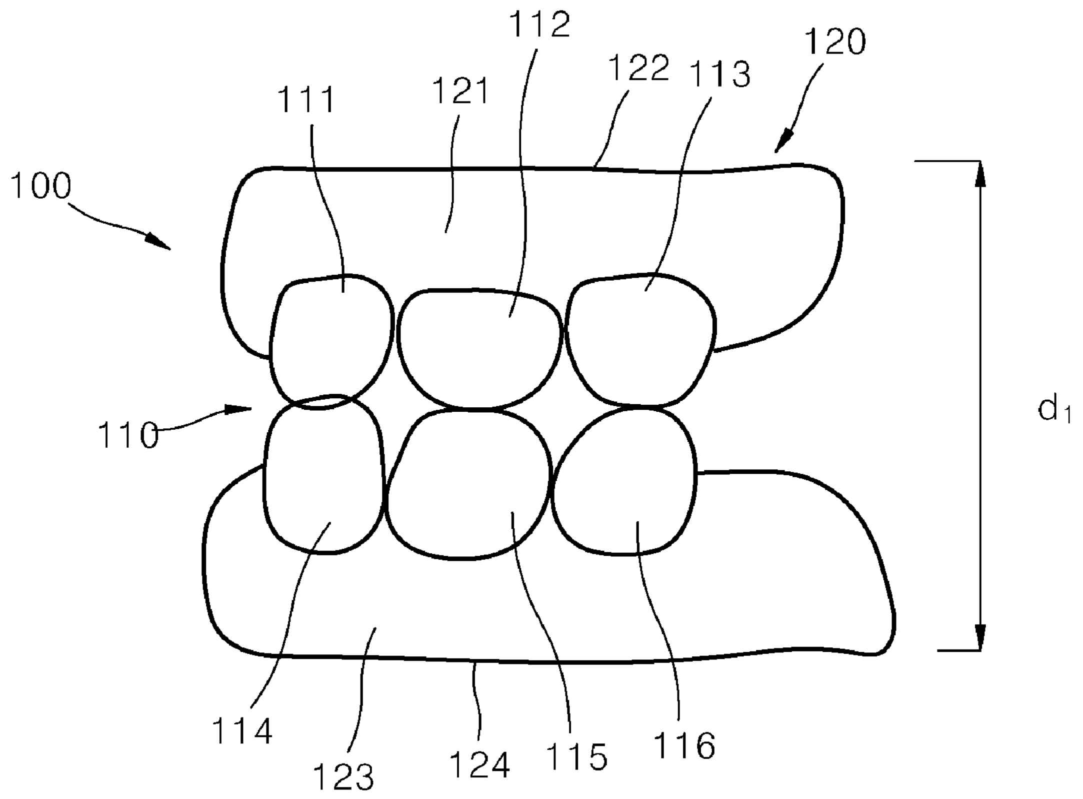
FIGS. 2 and 3 show comparative examples for comparison with the data processing method according to the present disclosure.
Figure 3:
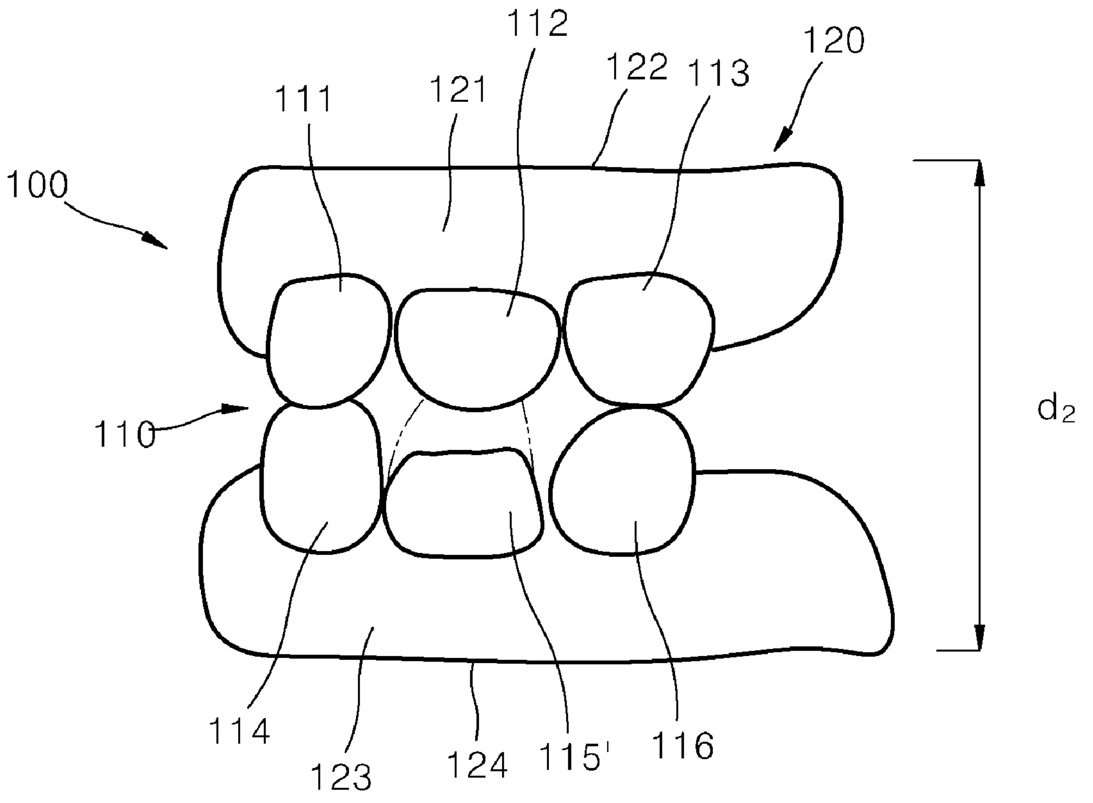

FIGS. 2 and 3 show comparative examples for comparison with the data processing method according to the present disclosure.

Referring to FIG. 2, exemplary comparison oral cavity data 100 for describing a comparative example is shown. The comparison oral cavity data 100 has comparison teeth 110, which may include, for example, a first comparison tooth 111, a second comparison tooth 112, a third comparison tooth 113, a fourth comparison tooth 114, a fifth comparison tooth 115, and a sixth comparison tooth 116. In addition, the first comparison tooth 111 may engage with the fourth comparison tooth 114; the second comparison tooth 112 may engage with the fifth comparison tooth 115; and the third comparison tooth 113 may engage with the sixth comparison tooth 116. On the other hand, the comparison oral cavity data 100 has a comparison gingiva 120, which may include a comparison upper jaw gingiva 121 corresponding to the gingiva of comparison upper jaw data and a comparison lower jaw gingiva 123 corresponding to the gingiva of the comparison lower jaw data. Each comparison gingiva may include the upper jaw oral cavity vestibule 122 and the lower jaw oral cavity vestibule 124, and the upper jaw oral cavity vestibule 122 and the lower jaw oral cavity vestibule 124 may be set through position information and curve information of the gingivae. Meanwhile, the first occlusal vertical dimension d1 may be measured through the distance between the upper jaw oral cavity vestibule 122 and the lower jaw oral cavity vestibule 124.

Referring to FIG. 3, among the comparison teeth 110, a fifth comparison tooth 115' after the medical procedure is shown. Due to the post-medical procedure fifth comparison tooth 115', the bite force of the patient after the medical procedure may be different from that of the patient before the medical procedure. More specifically, in FIG. 2, the total bite force is distributed between the first comparison tooth 111 and the fourth comparison tooth 114, between the second comparison tooth 112 and the fifth comparison tooth 115, and between the third comparison tooth 113 and the sixth comparison teeth 116. Contrarily, in FIG. 3, since the second comparison tooth 112 does not engage with the post-medical procedure fifth comparison tooth 115', the total bite force is distributed between the first comparison tooth 111 and the fourth comparison tooth 114, and between the third comparison tooth 113 and the sixth comparison tooth 116. Accordingly, the second occlusal vertical dimension d2, which is the distance between the upper jaw oral cavity vestibule 122 and the lower jaw oral cavity vestibule 124, may be smaller than the first occlusal vertical dimension d1.

Meanwhile, as described with reference to FIGS. 2 and 3, in the case where a dental prosthesis is designed based on the oral cavity data 100 including a post-medical procedure tooth (e.g., the post-medical procedure fifth comparison tooth), when the dental prosthesis is applied to the patient's oral cavity, the height of the dental prosthesis may not exactly fit it. Therefore, in order to design an accurate dental prosthesis, it is necessary for the user to consider various combinations of pre-medical procedure upper and lower jaw data, post-medical procedure upper and lower jaw data, occlusion data representing the occlusion structure in the pre-medical procedure upper and lower jaw data, and occlusion data representing the occlusion structure in the post-medical procedure upper and lower jaw data.

Figure 4:
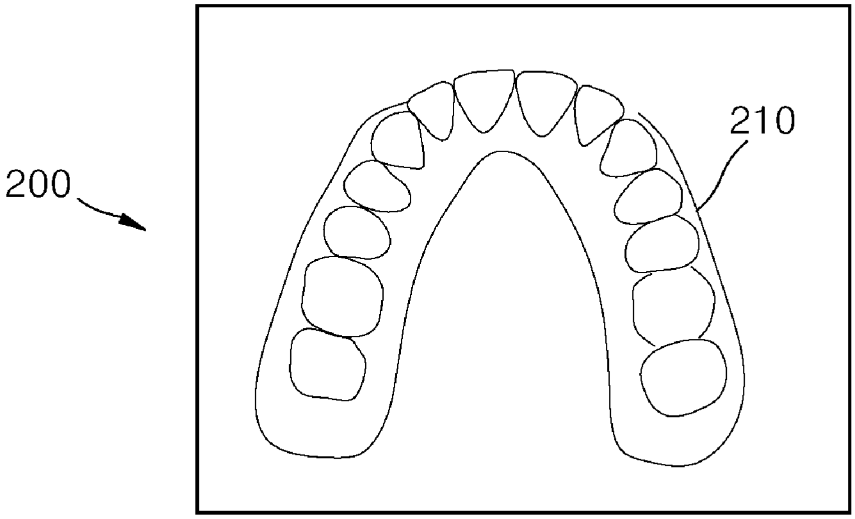
FIG. 4 is for explaining pre-medical procedure upper and lower jaw data.
Figure 4:
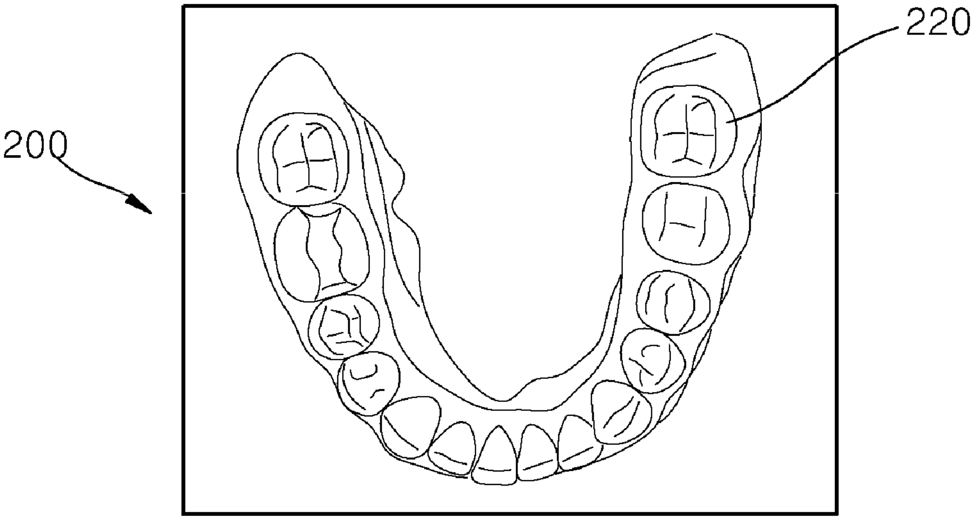
Figure 5:
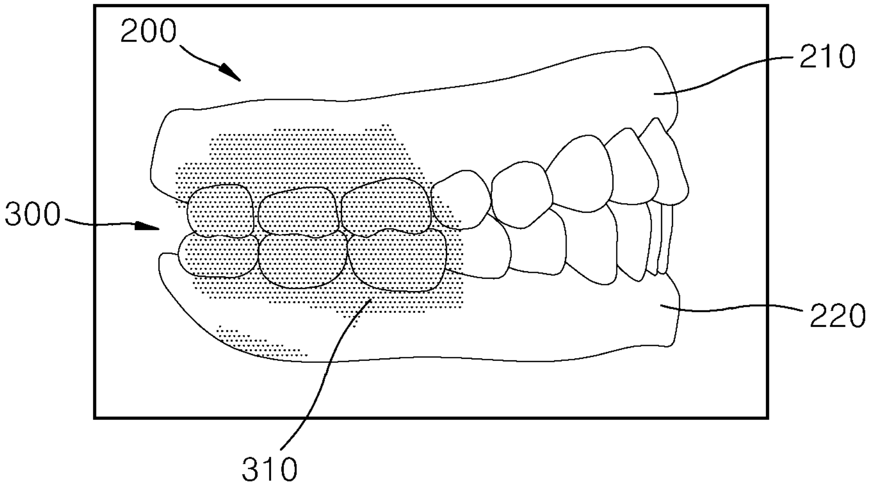
FIG. 5 is for explaining occlusion data.
Figure 5:
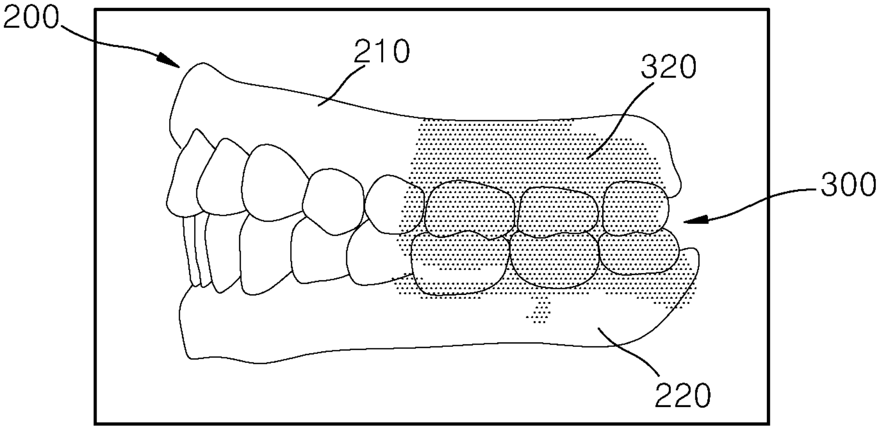

FIG. 4 is for explaining pre-medical procedure upper and lower jaw data 200. More specifically, FIG. 4(*a*) represents the pre-medical procedure upper jaw data 210, and FIG. 4(*b*) represents the pre-medical procedure lower jaw data 220. In addition, FIG. 5 is for explaining occlusion data 300. More specifically, FIG. 5(*a*) is for explaining one side occlusion data 310, and FIG. 5(*b*) is for explaining the other side occlusion data 320.

Referring to FIGS. 1, 4, and 5, the data processing method according to the present disclosure includes the step of obtaining scan data (S110). With regard to the step of obtaining scan data (S110), the scan data may include at least one set of upper and lower jaw data 200 and a plurality of sets of occlusion data 300 obtained by scanning the object. A digital model representing the object may be generated by combining the upper and lower jaw data 200 and the occlusion data 300 representing the occlusion shape by the upper and lower jaw data 200.

The object refers to one that is scanned to provide a dental prosthesis to a patient. By way of example, the object may be an actual oral cavity interior of a patient to which a dental prosthesis is applied. Alternatively, the object may be a dental impression model or a plaster model corresponding to the oral cavity of the patient.

Further, the upper and lower jaw data 200 may include upper jaw data 210 representing the patient's upper jaw and lower jaw data 220 representing the patient's lower jaw. That is, the upper and lower jaw data 200 may be interpreted as covering the upper jaw data 210 and the lower jaw data 220. The user may obtain the upper jaw data 210 and the lower jaw data 220 respectively by scanning the object. In some cases, the user may obtain both the upper jaw data 210 and the lower jaw data 220 in a single stage. In general, since the upper jaw data 210 and the lower jaw data 220 are formed separately, the user can obtain the upper and lower jaw data 200 in a single stage by using the characteristic that the upper jaw data 210 and the lower jaw data 220 are not aligned to each other.

Meanwhile, the upper and lower jaw data 200 may be obtained by scanning the object before a medical procedure. By way of example, the upper and lower jaw data 200 may include the upper jaw data 210 representing the pre-medical procedure upper jaw and the lower jaw data 220 representing the pre-medical procedure lower jaw. With this regard, the medical procedure may refer to tooth preparation. However, examples of the medical procedure may include, without limitation, at least one of all types of medical procedures for changing the shape, position, or direction of a tooth, such as tooth extraction, reattachment of a fractured tooth fragment, and the like.

In addition, the user may obtain the occlusion data 300 from the scan data. The occlusion data 300 may be obtained by scanning the buccal surfaces of the upper and lower jaws of the object, and the occlusion data 300 may include at least a portion of the upper jaw data 210 and at least a portion of the lower jaw data 220. One or more occlusion data 300 may be obtained. By way of example, the user may obtain one side occlusion data 310 by scanning one side surface of the upper jaw data 210 and one side surface of the lower jaw data 220. Based on the one side occlusion data 310, the upper jaw data 210 and the lower jaw data 220 may be aligned to obtain a digital model having a shape similar to that of the real object.

Also, the occlusion data 300 may be obtained by scanning various side surfaces of the object. By way of example, the user may obtain one side occlusion data 310 by scanning one side surface of the upper jaw data 210 and one side surface of the lower jaw data 220 (FIG. 5(*a*)), and may obtain the other side occlusion data 320 by scanning the other side surface of the upper jaw data 210 and the other side surface of the lower jaw data 220 (FIG. 5(*b*)). In this way, when the occlusion data 300 representing various side surfaces are obtained, the upper and lower jaw data 200 can be more accurately aligned through the occlusion data 300.

Also, a plurality of sets of occlusion data 300 may be obtained by scanning an object in different states. By way of example, the plurality of sets of occlusion data 300 may include first occlusion data obtained by scanning the buccal surface of the pre-medical procedure object, and second occlusion data obtained by scanning the post-medical procedure object. In this way, a plurality of alignment scan data in which the upper and lower jaw data 200 are aligned may be generated using the first occlusion data and the second occlusion data.

Figure 6:
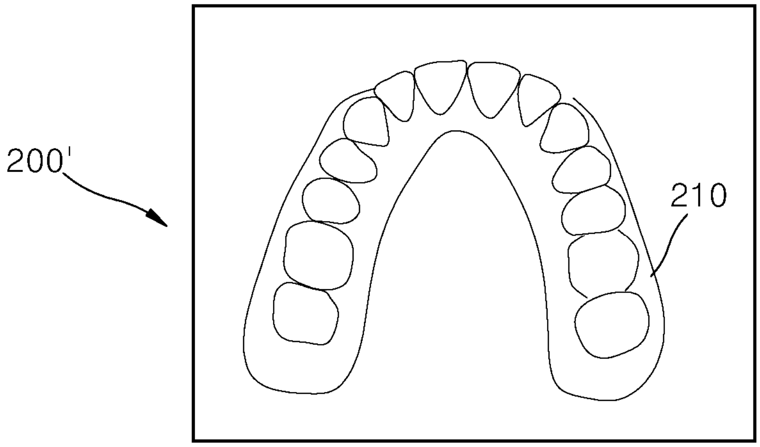
FIG. 6 is for explaining post-medical procedure upper and lower jaw data.
Figure 6:
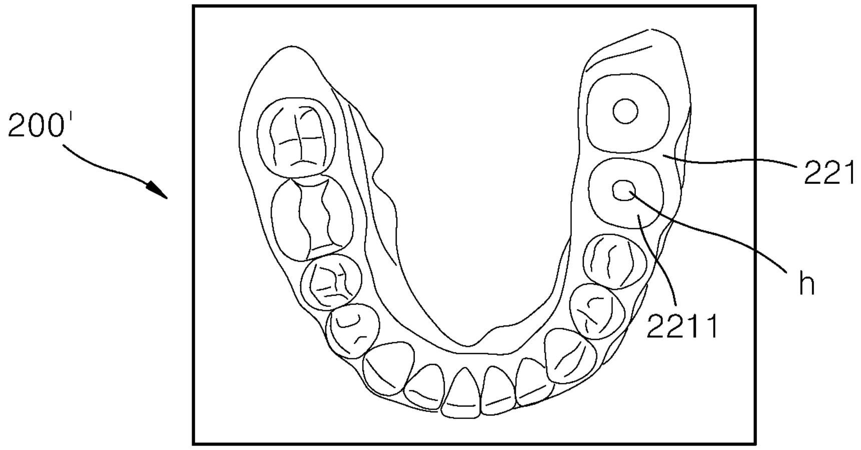

FIG. 6 is for explaining post-medical procedure upper and lower jaw data 200'. More specifically, FIG. 6(*a*) represents the pre-medical procedure upper jaw data 210, and FIG. 6(*b*) represents the post-medical procedure lower jaw data 221.

Referring to FIG. 6, the upper and lower jaw data 200' may also be obtained by scanning the post-medical procedure object. By way of example, the user may obtain the upper jaw data 210 representing the upper jaw before the medical procedure, and the post-medical procedure lower jaw data 221 representing the lower jaw after the medical procedure. In this case, the post-medical procedure lower jaw data 221 may include at least one set of medical procedure tooth data 2211 representing the post-medical procedure tooth. Therefore, a structure in which the post-medical procedure lower jaw data 221 and the pre-medical procedure upper jaw data 210 are occluded with each other may be different from a structure in which the pre-medical procedure lower jaw data 220 and the pre-medical procedure upper jaw data 210 are occluded with each other.

Meanwhile, the at least one set of medical procedure tooth data 2211 represents the shape of the tooth which has been subjected to the medical procedure, and when the medical procedure includes a process of tooth preparation of the inner portion of the tooth, the at least one set of medical procedure tooth data 2211 may include a hole h. Even if the patient's actual oral cavity interior is scanned or the plaster model is scanned, the interior of the hole h of the at least one set of medical procedure tooth data 2211 cannot be precisely scanned. In this case, in order to accurately scan the post-medical procedure lower jaw data 221 including the at least one set of medical procedure tooth data 2211, a dental impression model may be used.

In the foregoing discussion, it has been described without limitation that the post-medical procedure upper and lower jaw data 200' obtained by scanning the post-medical procedure object includes the post-medical procedure tooth in the post-medical procedure lower jaw data 221. By way of example, the post-medical procedure object may have a post-medical procedure tooth in the upper jaw or have a post-medical procedure tooth in the lower jaw. Alternatively, the post-medical procedure object may have post-medical procedure teeth in both the upper jaw and the lower jaw.

Hereinafter, a process of obtaining at least a portion of the upper and lower jaw data using a dental impression model will be described.

Figure 7:
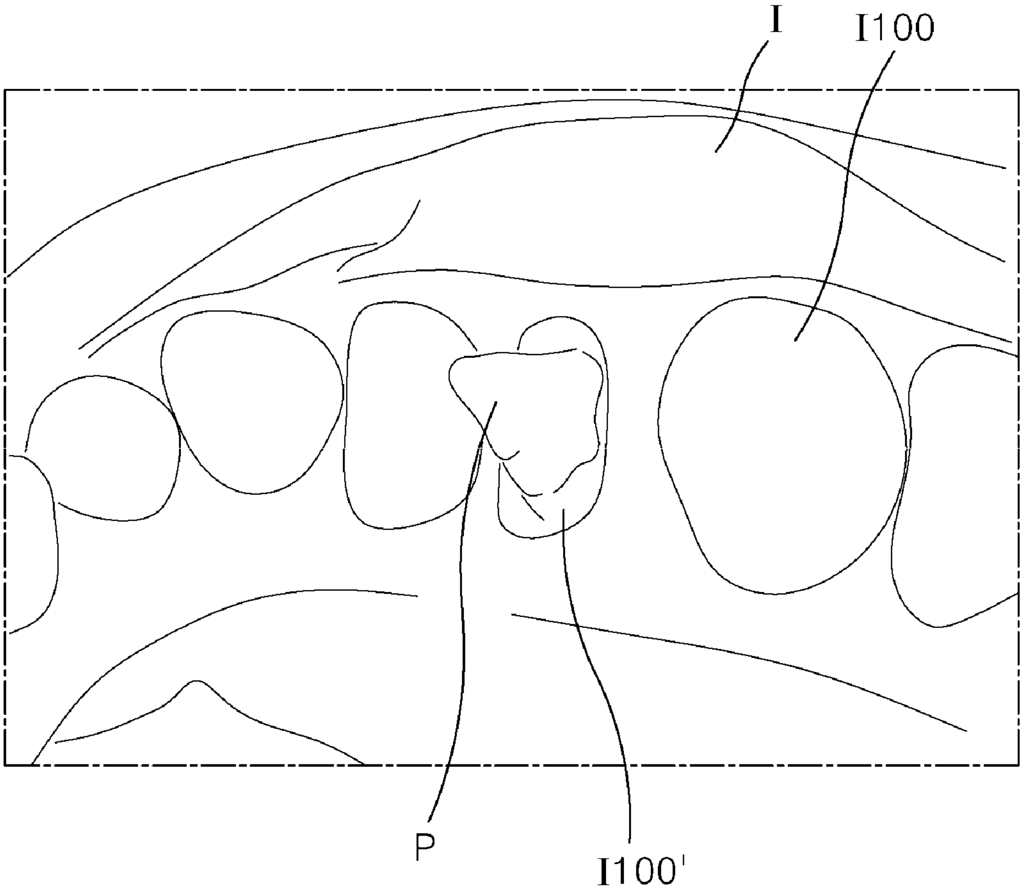
FIG. 7 is for explaining a dental impression model for obtaining post-medical procedure upper and lower jaw data.

FIG. 7 is for explaining a dental impression model I for obtaining post-medical procedure upper and lower jaw data. In this regard, the dental impression model I shown in FIG. 7 may be at least one of a dental impression upper jaw model obtained by applying an impression material to the patient's upper jaw and a dental impression lower jaw model obtained by applying an impression material to the patient's lower jaw.

Referring to FIGS. 6 and 7, in the step of obtaining scan data (S110), the upper and lower jaw data 200 may be obtained by scanning the patient's actual oral cavity interior, but it may also be obtained by scanning the dental impression model and/or the plaster model as described above. By way of example, the upper and lower jaw data 200 may be obtained by scanning the upper jaw model and the lower jaw model represented by the plaster model. In another example, the upper and lower jaw data 200 may be obtained by scanning a dental impression upper jaw model and a dental impression lower jaw model expressed by the dental impression model. When the upper and lower jaw data 200 is obtained by scanning the dental impression upper jaw model and the dental impression lower jaw model, the upper and lower jaw data 200 may obtain at least a portion of the impression upper and lower jaw data by scanning the dental impression model I. In this case, the dental impression model I may include a dental impression tooth model 1100 and at least one dental impression medical procedure tooth model 1100' corresponding to at least one set of medical procedure tooth data 2211. When obtaining the dental impression model I, the impression material may be filled into the hole h of the tooth which has been subjected to the medical procedure such that the hole h is formed therein, and the at least one dental impression medical procedure tooth model 1100' may include a protrusion P corresponding to the hole h. The user may obtain the impression upper and lower jaw data by scanning the dental impression model I using the scan unit, and may obtain the upper and lower jaw data expressing the same shape as the patient's oral cavity shape by reversing the impression upper and lower jaw data. At this time, the shape of the protrusion P may be reversed to be expressed as a recessed shape inside the hole h, and the interior of the hole h of the at least one set of medical procedure tooth data 2211 may be accurately represented by data obtained by scanning the dental impression model I.

Meanwhile, the upper and lower jaw data 200 may be obtained by complexly scanning an engraved object such as the dental impression model I and an embossed object such as a plaster model and a patient's actual oral cavity interior in a combination manner. By way of example, it is assumed that the medical procedure tooth is present in the lower jaw of the object. In this case, in order to obtain the post-medical procedure upper and lower jaw data 200', the embossed object may be scanned to obtain the upper jaw data among the post-medical procedure upper and lower jaw data 200', and the engraved object may be scanned to obtain the lower jaw data among the post-medical procedure upper and lower jaw data 200'. In another example, in order to obtain the post-medical procedure upper and lower jaw data 200', the engraved object may be scanned to obtain the post-medical procedure upper and lower jaw data 200'. The occlusion data may be obtained by scanning the buccal surface of the embossed object, and the upper and lower jaw data (or the post-medical procedure upper and lower jaw data) may be aligned by the occlusion data to generate alignment scan data.

In this way, by scanning the engraved object including the dental impression model I and obtaining at least a portion of the upper and lower jaw data, there is an advantage in that it is possible to accurately obtain the shape of the medical procedure tooth of the object, which is difficult to obtain by scanning the embossed object. In particular, by scanning the engraved object including the dental impression model I, at least one set of medical procedure tooth data 2211 of the post-medical procedure upper and lower jaw data 200' can be accurately obtained.

Figure 8:
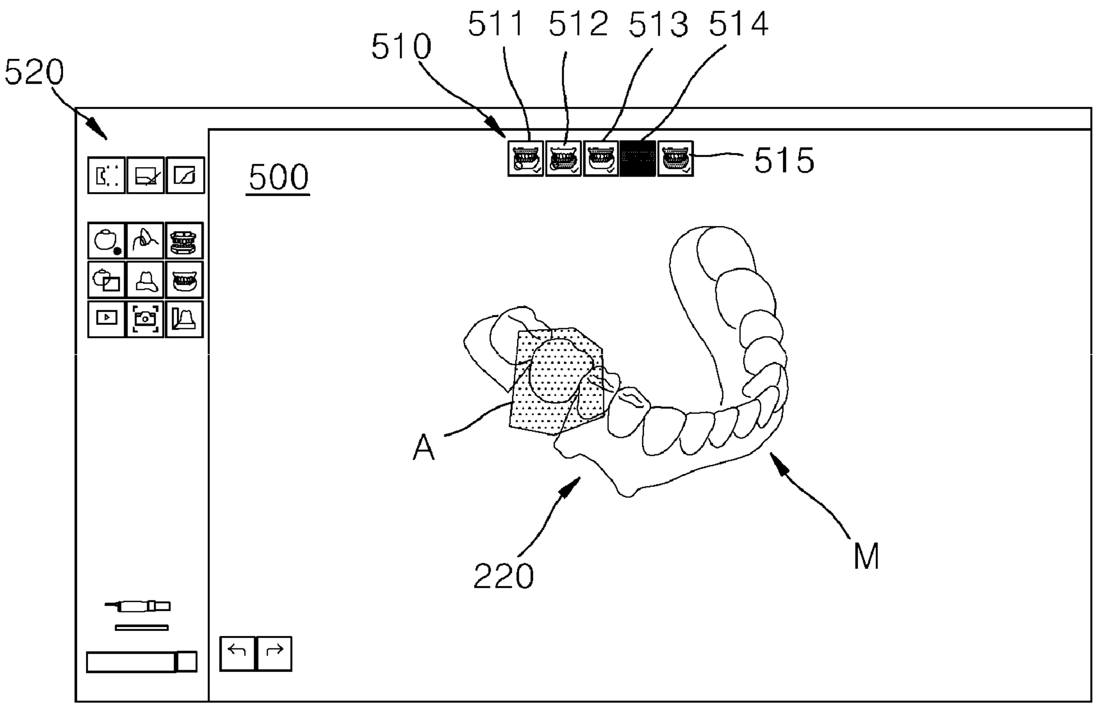
FIG. 8 is for explaining a process of digitally trimming a portion of the obtained scan data.

FIG. 8 is for explaining a process of digitally trimming a portion of the obtained scan data.

Referring to FIG. 8, the upper and lower jaw data 200 obtained by scanning the post-medical procedure object may be obtained by first scanning the pre-medical procedure object to obtain a digital model M, trimming the part corresponding to the post-medical procedure tooth and scanning the corresponding part of the post-medical procedure object. By way of example, the lower jaw data 220 is displayed in the form of the digital model M on the screen of the user interface 500. A stage selection unit 510 may be formed on one side of the screen of the user interface 500. The stage selection unit 510 may include a pre-medical procedure upper jaw data scan stage 511, a pre-medical procedure lower jaw data scan stage 512, a post-medical procedure upper jaw data scan stage 513, and a post-medical procedure lower jaw data scan stage 514, and an occlusion data scan stage 515. The user may obtain the digital model M by scanning a part of the object corresponding to each of the stages 511, 512, 513, 514, and 515. By way of example, in the pre-medical procedure upper jaw data scan stage 511, the user may obtain the pre-medical procedure upper jaw data by scanning the upper jaw part of the pre-medical procedure object. In addition, in the post-medical procedure upper jaw data scan stage 512, the user may obtain the post-medical procedure upper jaw data by scanning the upper jaw part of the post-medical procedure object. In addition, in the pre-medical procedure lower jaw data scan stage 513, the user may obtain the pre-medical procedure lower jaw data by scanning the lower jaw part of the pre-medical procedure object. Also, in the post-medical procedure lower jaw data scan stage 514, the user may obtain the post-medical procedure lower jaw data. Also, in the occlusion data scan stage 515, the user may obtain at least one set of occlusion data by scanning the buccal surface of the object.

A tool box 520 may be formed on another side of the screen of the user interface 500. The tool box 520 has various buttons arranged therein for editing and analyzing a plurality of sets of data, and the tool box 520 enables user operations such as polygonally selecting and trimming a predetermined portion of scan data, setting a margin line, performing calibration of a scan unit (or 3D scanner), and the like.

In the post-medical procedure lower jaw data scan stage 514, the user may select a trimming button among the buttons arranged in the tool box 520, and may designate a portion of the lower jaw data 220 corresponding to the post-medical procedure tooth as the trimming region A. The portion of the lower jaw data 220 designated as the trimming region A may be deleted.

Figure 9:
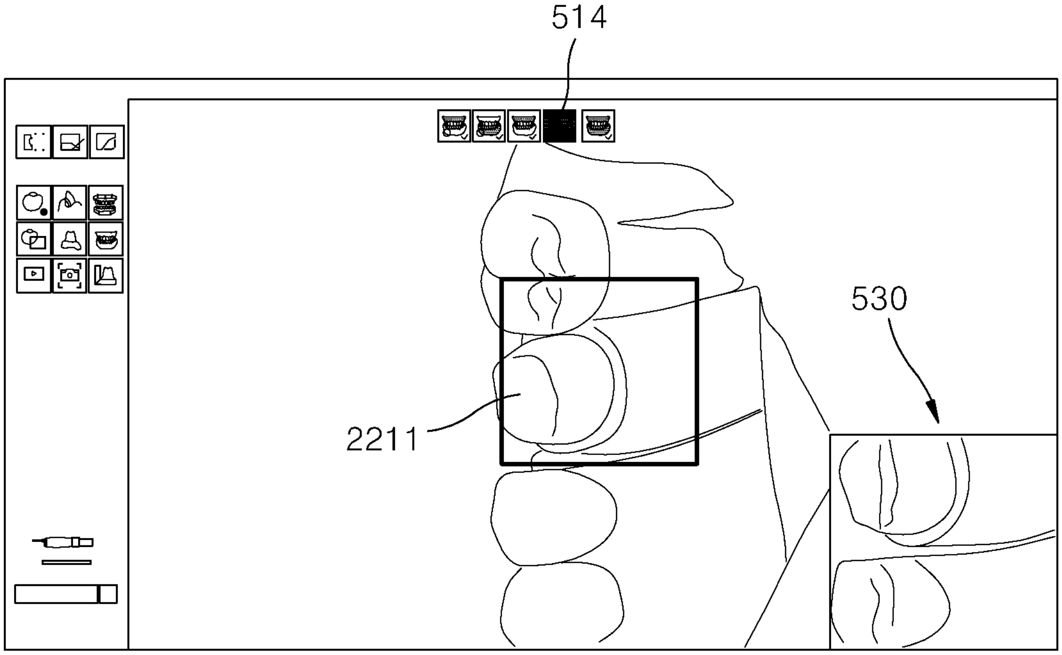
FIG. 9 is for explaining a scan process performed to obtain post-medical procedure lower jaw data.

FIG. 9 is for explaining a scan process performed to obtain the post-medical procedure lower jaw data 221.

Referring to FIG. 9, in the lower jaw data 220 from which the trimming region A has been deleted, the post-medical procedure lower jaw may be scanned to obtain the post-medical procedure lower jaw data 221 including the medical procedure tooth data 2211. The scan process may be displayed in real time through a live screen 530, and the medical procedure tooth data 2211 may be combined with the lower jaw data 220 while filling the trimming region A to be formed as the post-medical procedure lower jaw data 221.

Thus, the following advantage can be achieved: even if the entire post-medical procedure object is not scanned, the post-medical procedure upper and lower jaw data 200' can be obtained conveniently by scanning a part of the post-medical procedure object, based on the upper and lower jaw data 200 obtained by scanning the pre-medical procedure object.

Figure 10:
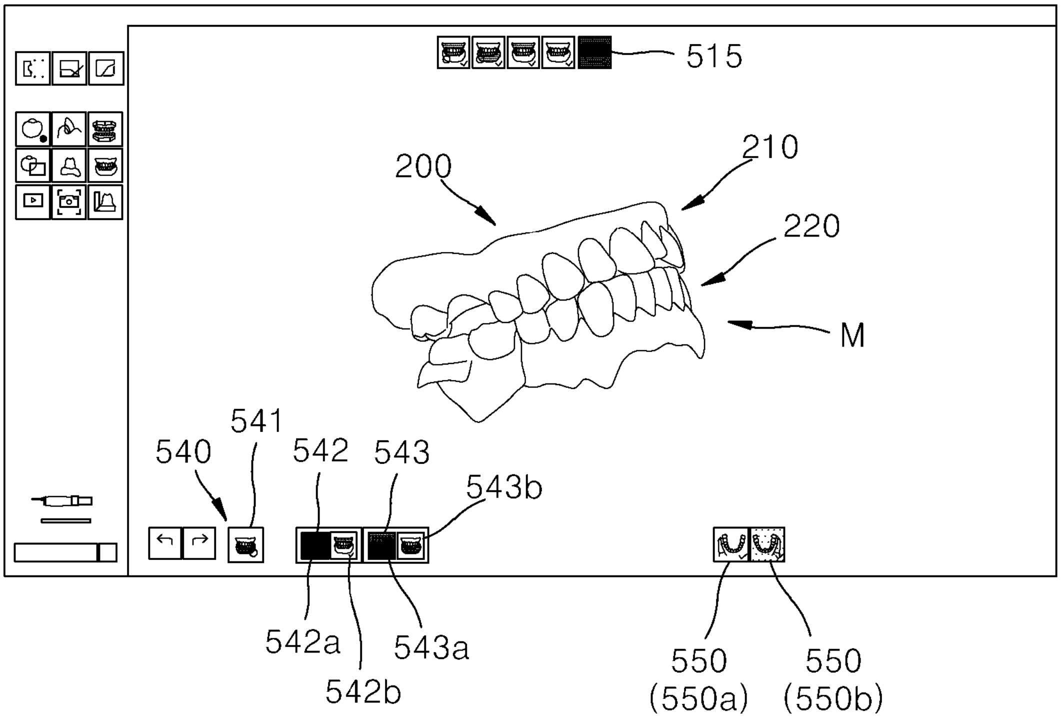
FIGS. 10 and 11 are for explaining upper and lower jaw data representing a pre-medical procedure object, and upper and lower jaw data representing a post-medical procedure object.
Figure 11:
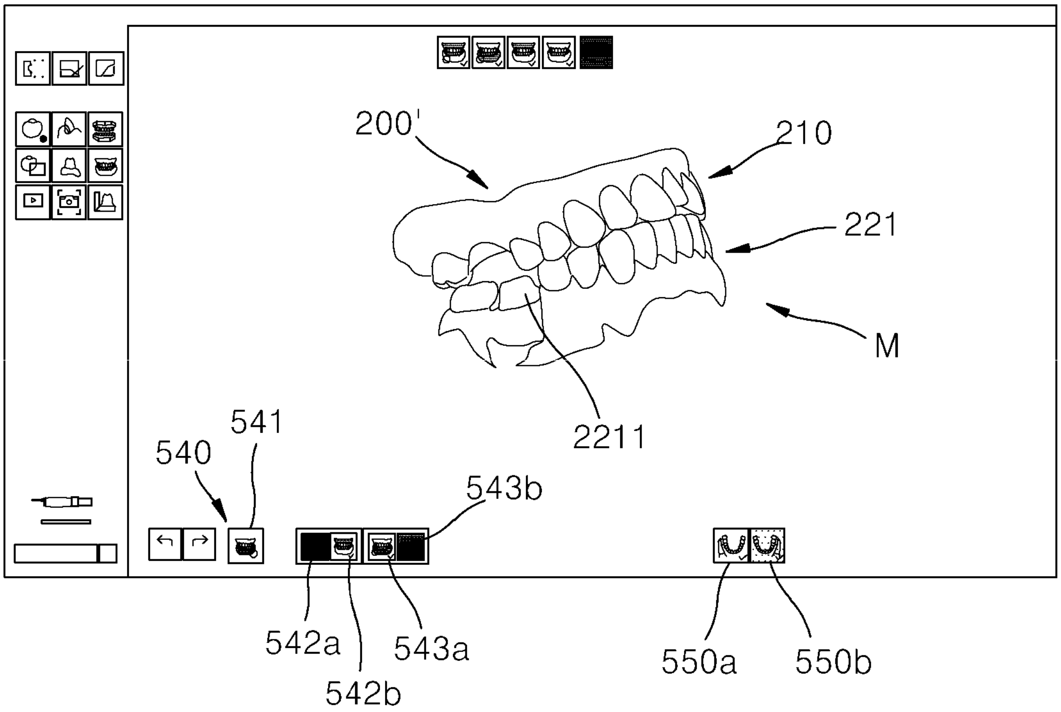

FIGS. 10 and 11 are for explaining the upper and lower jaw data 200 representing a pre-medical procedure object and the post-medical procedure upper and lower jaw data 200' representing a post-medical procedure object.

The data processing method according to the present disclosure includes obtaining a plurality of sets of alignment scan data (S120). The step of obtaining a plurality of sets of alignment scan data (S120) may include aligning the upper and lower jaw data 200 to each of different sets of occlusion data 300 among the plurality of sets of the occlusion data 300.

The step of obtaining a plurality of sets of alignment scan data (S120) will be described in more detail with reference to the related drawings. Referring to FIG. 10, the digital model M shown in FIG. 10 may be the upper and lower jaw data 200 including the upper jaw data 210 representing the pre-medical procedure upper jaw and the lower jaw data 220 representing the pre-medical procedure lower jaw. In this case, the upper and lower jaw data 200 may be aligned based on first occlusion data obtained by scanning the pre-medical procedure object. Referring to FIG. 11, the digital model M shown in FIG. 11 may be the post-medical procedure upper and lower jaw data 200' including the upper jaw data 210 representing the pre-medical procedure upper jaw and the post-medical procedure lower jaw data 221 representing the post-medical procedure lower jaw.

Meanwhile, the upper and lower jaw data 200 of the displayed digital model M may select through an upper jaw selection unit 542 and a lower jaw selection unit 543 any one of what has been obtained by scanning the pre-medical procedure object or what has been obtained by scanning the post-medical procedure object. By way of example, the upper and lower jaw data 200 of the digital model M shown in FIG. 10 may include the upper jaw data 210 and the lower jaw data 220, both of which have been obtained by scanning the pre-medical procedure object and selected, respectively, through a pre-medical procedure upper jaw selection unit 542*a* and a pre-medical procedure lower jaw selection unit 543*a*. In addition, in the post-medical procedure upper and lower jaw data 200' of the digital model M shown in FIG. 11, through the pre-medical procedure upper jaw selection unit 542*a* and the post-medical procedure lower jaw selection unit 543*b*, the upper jaw data 210 may be what has been obtained by scanning the pre-medical procedure object, and the post-medical procedure lower jaw data 221 may be what has been obtained by scanning the post-medical procedure object. Meanwhile, the digital model M shown in FIG. 11 may include the post-medical procedure lower jaw data 221 having the medical procedure tooth data 2211. By way of example, the digital model M shown in FIG. 11 may be first alignment scan data obtained by aligning the upper and lower jaw data 200 obtained by scanning the post-medical procedure object to the first occlusion data obtained by scanning the buccal surface of the pre-medical procedure object.

Figure 13:
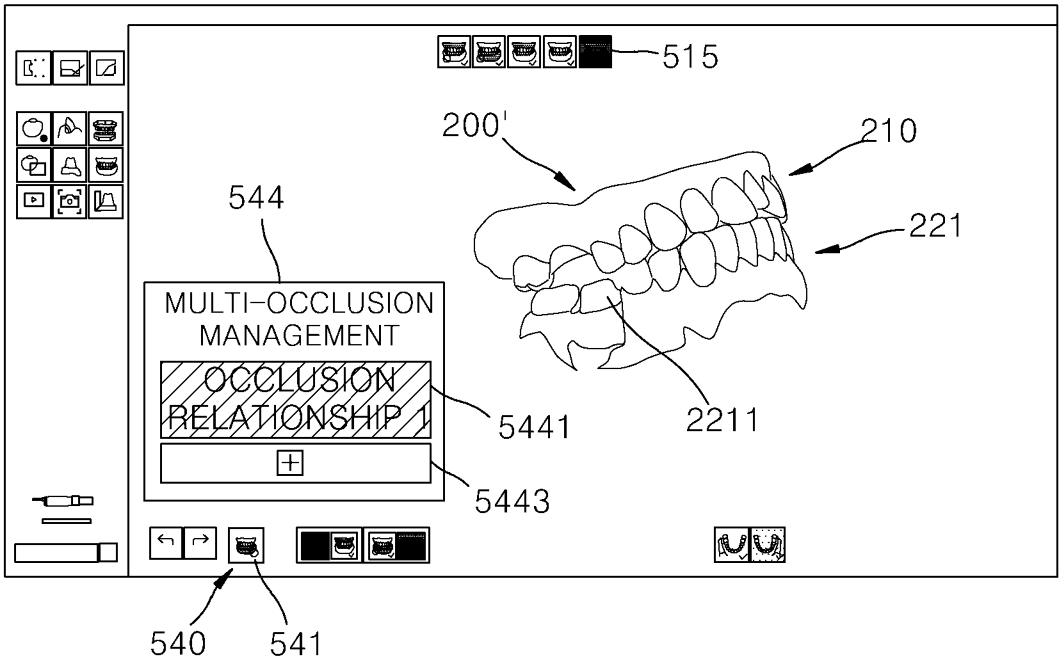
FIG. 13 is for explaining a process of setting multiple occlusions.
Figure 14:
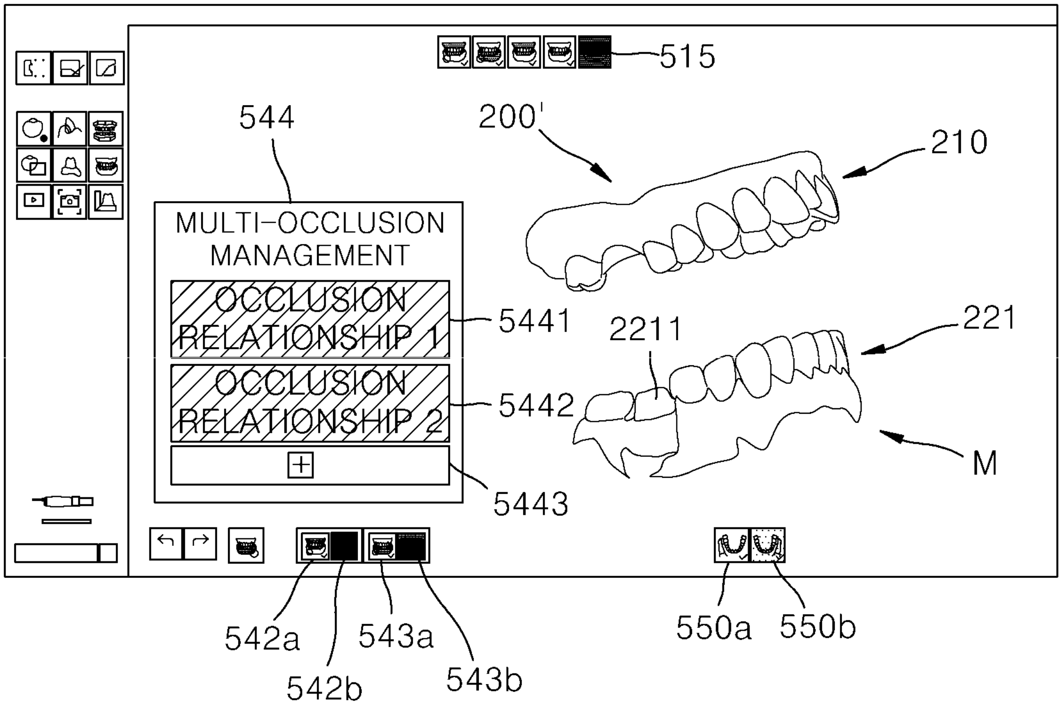
FIG. 14 is for explaining a process of generating new alignment scan data.

FIG. 12 is for explaining the alignment scan data which may be generated by the combination of the occlusion data and the upper and lower jaw data, FIG. 13 is for explaining a process of setting multiple occlusions, and FIG. 14 is for explaining a process of generating new alignment scan data.

Referring to FIG. 12, a plurality of exemplary alignment scan data which may be obtained in the data processing method according to the present disclosure is shown. By way of example, the first alignment scan data may be generated by aligning the first occlusion data obtained by scanning the buccal surface of the pre-medical procedure object with the upper and lower jaw data obtained by scanning the post-medical procedure object. Also, the second alignment scan data may be generated by aligning the second occlusion data obtained by scanning the buccal surface of the post-medical procedure object with the upper and lower jaw data obtained by scanning the post-medical procedure object. Also, the third alignment scan data may be generated by aligning the first occlusion data obtained by scanning the buccal surface of the pre-medical procedure object with the upper and lower jaw data obtained by scanning the pre-medical procedure object. Also, the fourth alignment scan data may be generated by aligning the second occlusion data obtained by scanning the buccal surface of the post-medical procedure object with the upper and lower jaw data obtained by scanning the pre-medical procedure object. Meanwhile, each alignment scan data may be expressed in the form of a digital model, and an occlusal vertical dimension for each alignment scan data may be measured. In addition, according to the contents shown in FIG. 12, it is described that the alignment scan data can be generated in four types, but there is no restriction thereto. If necessary, the upper jaw data may be divided into pre- and post-medical procedure ones, and the lower jaw data may be divided into pre- and post-medical procedure ones, so that eight types of alignment scan data may be generated. Also, depending on the type of medical procedure, a plurality of sets of upper jaw data, a plurality of sets of lower jaw data, and a plurality of sets of occlusion data may be obtained, and accordingly, the number of sets of alignment scan data may be further increased.

Referring to FIGS. 13 and 14, a multi-occlusion management unit 540 may be displayed on the screen of the user interface 500. The multi-occlusion management unit 540 may generate a plurality of sets of alignment scan data by combining different upper and lower jaw data 200 and/or different occlusion data 300. A multi-occlusion management window 544 which appears by selecting the multi-occlusion management unit 540 may display the generated alignment scan data in a list represented as 'occlusion relationship'. As shown in FIG. 13, first alignment scan data in which the upper and lower jaw data 200 obtained by scanning the post-medical procedure object is aligned with the first occlusion data is displayed as a first occlusion relationship 5441. Meanwhile, the user may select an occlusion relationship adding unit 5443 represented by the symbol '+' to generate alignment scan data (second alignment scan data, third alignment scan data, and the like) different from the first alignment scan data.

A process of obtaining second alignment scan data will be described with reference to FIG. 14. In the newly generated second occlusion relationship 5442, the user may determine, by using the upper jaw selection unit 542 and the lower jaw selection unit 543, whether to use the upper and lower jaw data 200 obtained by scanning the pre-medical procedure object or to use the post-medical procedure upper and lower jaw data 200' obtained by scanning the post-medical procedure object.

Thereafter, the occlusion data 300 may be obtained by selecting the occlusion scan unit 550. The occlusion scan unit 550 may include one side occlusion scan unit 550*a* and the other side occlusion scan unit 550*b*. By scanning at least two buccal surfaces to obtain one side occlusion data and the other side occlusion data, the upper and lower jaw data 200 (including at least one of the pre-medical procedure upper and lower jaw data and the post-medical procedure upper and lower jaw data 200') may be more precisely aligned.

Figure 15:
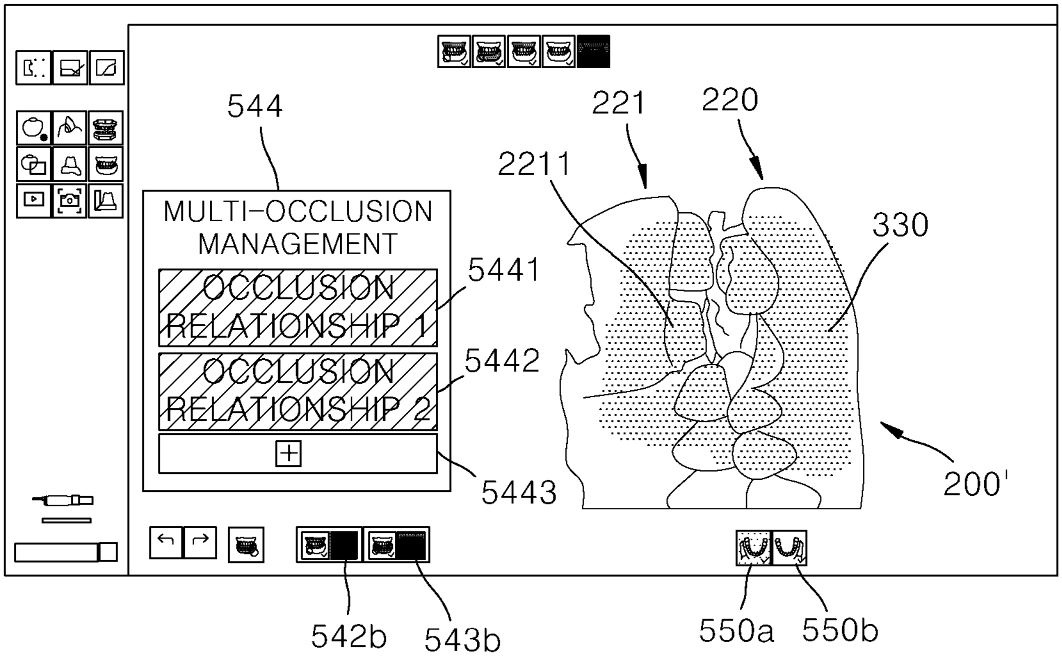
FIGS. 15 and 16 are for explaining a process of obtaining occlusion data in order to generate new alignment scan data.
Figure 16:
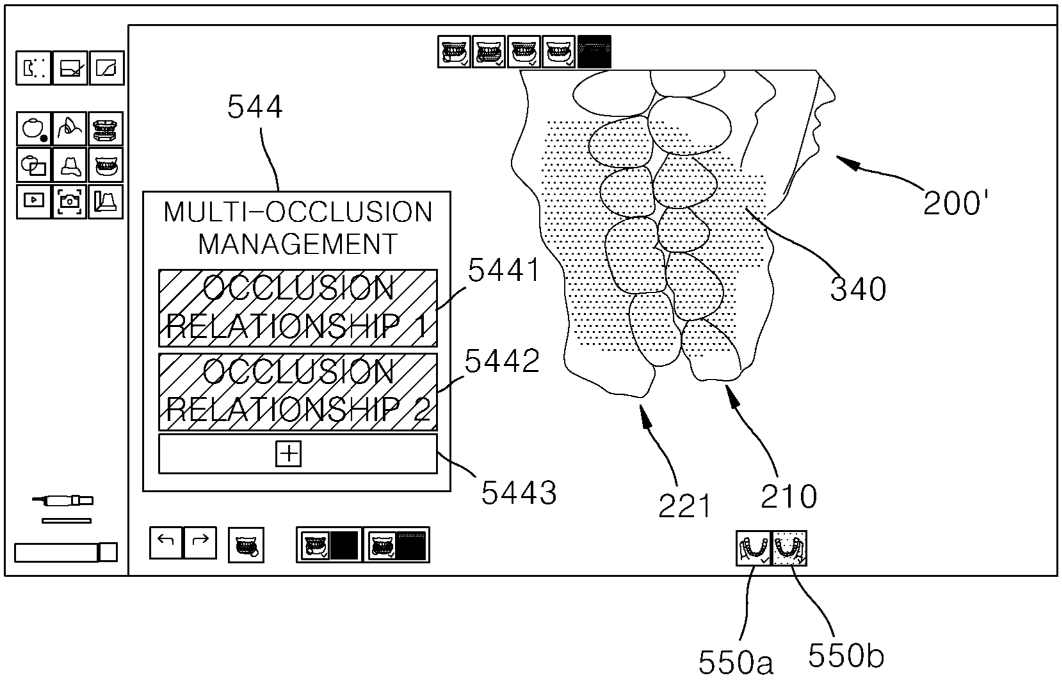

FIGS. 15 and 16 are for explaining a process of obtaining occlusion data in order to generate new alignment scan data.

Referring to FIG. 15, the user may obtain occlusion data 300 by selecting the one side occlusion scan unit 550*a* and scanning the buccal surface of the object. As shown in FIG. 15, the occlusion data 300 may be one side second occlusion data 330 of two sets of second occlusion data 330 and 340 obtained by scanning the buccal surfaces of the post-medical procedure object. The one side second occlusion data 330 may represent at least a portion of the post-medical procedure tooth data 2211. Referring to FIG. 16, the user may obtain the occlusion data 300 by selecting the other side occlusion scan unit 550*b* and scanning the other buccal surface of the object. As shown in FIG. 16, the occlusion data 300 may be the other side second occlusion data 340 of two sets of second occlusion data 330 and 340.

By obtaining the second occlusion data 330 and 340 as described above, the second alignment scan data in which the upper and lower jaw data 200 obtained by scanning the post-medical procedure object are aligned with the second occlusion data 330 and 340 can be generated. The second alignment scan data may represent a state in which the post-medical procedure object is occluded.

Meanwhile, the user may further generate additional alignment scan data through the multi-occlusion management unit 540. By way of example, the plurality of sets of alignment scan data may include third alignment scan data obtained by aligning the upper and lower jaw data 200 obtained by scanning the pre-medical procedure object to the first occlusion data, and fourth alignment scan data obtained by aligning the upper and lower jaw data 200 obtained by scanning the pre-medical procedure object to the second occlusion data.

The first alignment scan data obtained by aligning the upper and lower jaw data 200 obtained by scanning the post-medical procedure object with the first occlusion data obtained by scanning the buccal surface of the pre-medical procedure object can express the most ideal fit to which the dental prosthesis is applied, and can be considered when designing the outer surface of the dental prosthesis (for example, the contact surface with adjacent tooth or antagonist tooth). In addition, the second alignment scan data obtained by aligning the upper and lower jaw data 200 obtained by scanning the post-medical procedure object with the second occlusion data obtained by scanning the buccal surface of the post-medical procedure object can be considered by the user to determine the patient's oral cavity condition after the medical procedure. In addition, the third alignment scan data obtained by aligning the upper and lower jaw data 200 obtained by scanning the pre-medical procedure object with the first occlusion data obtained by scanning the buccal surface of the pre-medical procedure object can be considered when designing the inner surface of the dental prosthesis (for example, the contact surface with the preparation tooth). In addition, the fourth alignment scan data obtained by aligning the upper and lower jaw data 200 obtained by scanning the pre-medical procedure object with the second occlusion data obtained by scanning the buccal surface of the post-medical procedure object can express the degree of overlap or separation of the upper jaw data and the lower jaw data due to the changed bite force after the medical procedure, and can be considered when designing the outer surface of the dental prosthesis. Meanwhile, the degree of overlap or separation between the upper jaw data and the lower jaw data in the fourth alignment scan data may be expressed in the form of a color map.

By generating a plurality of sets of alignment scan data as described above, the following advantage can be achieved: the user can provide a more precisely designed dental prosthesis to the patient and provide optimal treatment to the patient.

After the step of obtaining a plurality of sets of alignment scan data (S120), the step of measuring the occlusal vertical dimensions of the plurality of sets of alignment scan data (S130) may be performed. The step of measuring the occlusal vertical dimensions (S130) may include measuring the occlusal vertical dimensions of a plurality of sets of alignment scan data aligned by the first occlusion data or the second occlusion data. The occlusal vertical dimension may be a distance between the oral cavity vestibules of the upper and lower jaw data 200. The upper and lower jaw data 200 may be aligned by the first occlusion data or the second occlusion data applied to each of the plurality of sets of alignment scan data. When the upper and lower jaw data 200 are aligned, the positions, directions or the like of the upper jaw data 210 and the lower jaw data 220 may be adjusted. By adjusting the positions or directions of the upper jaw data 210 and the lower jaw data 220, the positions of the upper jaw oral cavity vestibule and the lower jaw oral cavity vestibule may also be adjusted, and accordingly, the occlusal vertical dimension, which is the distance between the oral cavity vestibules, may also be changed. By way of example, different sets of alignment scan data may have different occlusal vertical dimensions.

Meanwhile, the occlusal vertical dimension may be measured based on at least one of location information and curve information of the upper and lower jaw data 200. By way of example, the occlusal vertical dimension may be measured based on the curve information of the upper jaw data 210 and the curve information of the lower jaw data 220, and each curve information may represent a concave portion of each of the upper jaw data 210 and the lower jaw data 220 as a curve value. Accordingly, the part with the largest curve value can be determined as the oral cavity vestibule, which is the most concave part of the upper jaw data 210 or the lower jaw data 220, and a separation distance between a part having the largest curve value of the upper jaw data 210 and a part having the largest curve value of the lower jaw data 220 may be determined as the occlusal vertical dimension.

The occlusal vertical dimension may be additionally measured based on location information. By way of example, the occlusal vertical dimension may be determined by a separation distance between portions with the largest curve values among the gingival part formed on the upper part of the upper jaw incisor among the gingival parts of the upper and lower jaw data 200 and the gingival part formed on the lower part of the lower jaw incisor. Accordingly, it is possible to prevent a problem, i.e., the inclined measurement of the occlusal vertical dimension unlike intended.

Also, the data processing method according to the present disclosure may include comparing a plurality of sets of alignment scan data (S140). In the comparing step (S140), the plurality of sets of alignment scan data of which the occlusal vertical dimensions have been measured may be compared to each other. By way of example, in the comparing step (S140), the magnitudes of the occlusal vertical dimensions, which the plurality of sets of alignment scan data have respectively, may be compared to each other. In this case, since the alignment scan data having a relatively large occlusal vertical dimension is generated based on the pre-medical procedure occlusion data, the dental prosthesis can be designed based on the alignment scan data having a relatively large occlusal vertical dimension. Accordingly, there is the advantage of being able to allow the user to provide the patient with a precise dental prosthesis reflecting consideration for the degree of contact with the patient's antagonist tooth.

Figure 17:
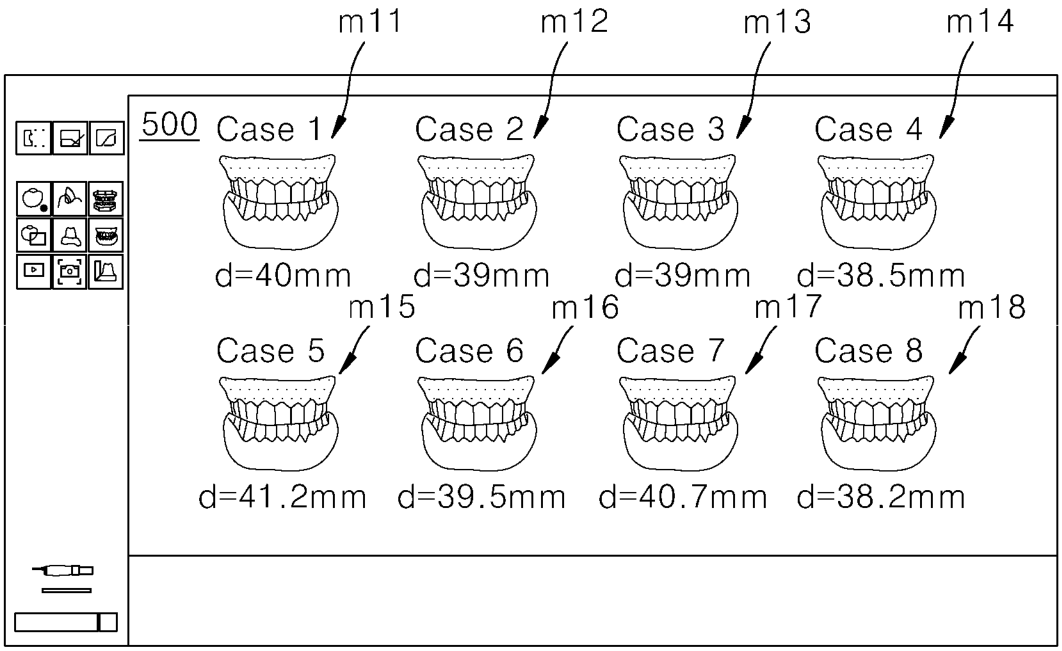
FIG. 17 represents a user interface screen on which various alignment scan data are displayed.

FIG. 17 represents a user interface screen on which various alignment scan data are displayed.

Referring to FIG. 17, the displaying step (S150) may be performed. In the displaying step (S150), various sets of alignment scan data are displayed in the form of a digital model (M). By way of example, the first to eighth models m11, m12, m13, m14, m15, m16, m17, and m18 may be simultaneously displayed on one screen of the user interface 500. In addition, on one side of each of the models m11, m12, m13, m14, m15, m16, m17, and m18 representing a plurality of sets of alignment scan data, the occlusal vertical dimension d of each alignment scan data may be displayed together. The user can easily compare to each other and check the shapes of the models m11, m12, m13, m14, m15, m16, m17, and m18 representing the plurality of sets of alignment scan data, and the measured values of the occlusal vertical dimensions d displayed together. By way of example, the fourth alignment scan data, in which the upper and lower jaw data obtained by scanning the pre-medical procedure object are aligned based on the second occlusion data, may indicate collision between the antagonist tooth and the tooth to be subjected to the medical procedure, which can easily indicate to the user that the second occlusion data is unsuitable for designing and providing a precise dental prosthesis. Such suitableness or unsuitableness can also be made known through the measured value of occlusal vertical dimension d.

Additionally, since the plurality of sets of alignment scan data and their occlusal vertical dimensions can be displayed on the screen of the user interface 500, the user can compare the occlusal vertical dimensions to each other without running a separate application. Therefore, since the user can compare a plurality of sets of alignment scan data at once using the data processing method according to the present disclosure, there is an advantage of being able to improve user convenience.

Also, the data processing method according to the present disclosure may further include the step of designing a dental prosthesis (S160). By way of example, the step of designing a dental prosthesis (S160) may include designing the dental prosthesis based on the first alignment scan data. That is, since the first alignment scan data in which the shapes of the upper and lower jaw data 200 having the post-medical procedure teeth are aligned with the first occlusion data based on the upper and lower jaw data 200 having the pre-medical procedure teeth are the optimal alignment scan data for designing the dental prosthesis, the dental prosthesis may be designed based on the first alignment scan data. According to FIG. 17, among the models m11, m12, m13, m14, m15, m16, m17 and m18 representing a plurality of sets of alignment scan data, the fifth model m15 with the largest occlusal vertical dimension may be the first alignment scan data.

Meanwhile, in the data processing method according to the foregoing description, the upper and lower jaw data are obtained first, and then the occlusion data are obtained, but the sequence is not limited to the above-described one. As another example, in the data processing method according to another embodiment of the present disclosure, occlusion data may be obtained first, and then upper and lower jaw data may be obtained by scanning pre- (and post-) medical procedure object.

Hereinafter, a data processing apparatus for performing the above-described data processing method according to the present disclosure will be described. In describing the data processing apparatus according to the present disclosure, the contents which have already described in the data processing method according to the present disclosure are briefly mentioned or repeated descriptions are omitted.

Figure 18:
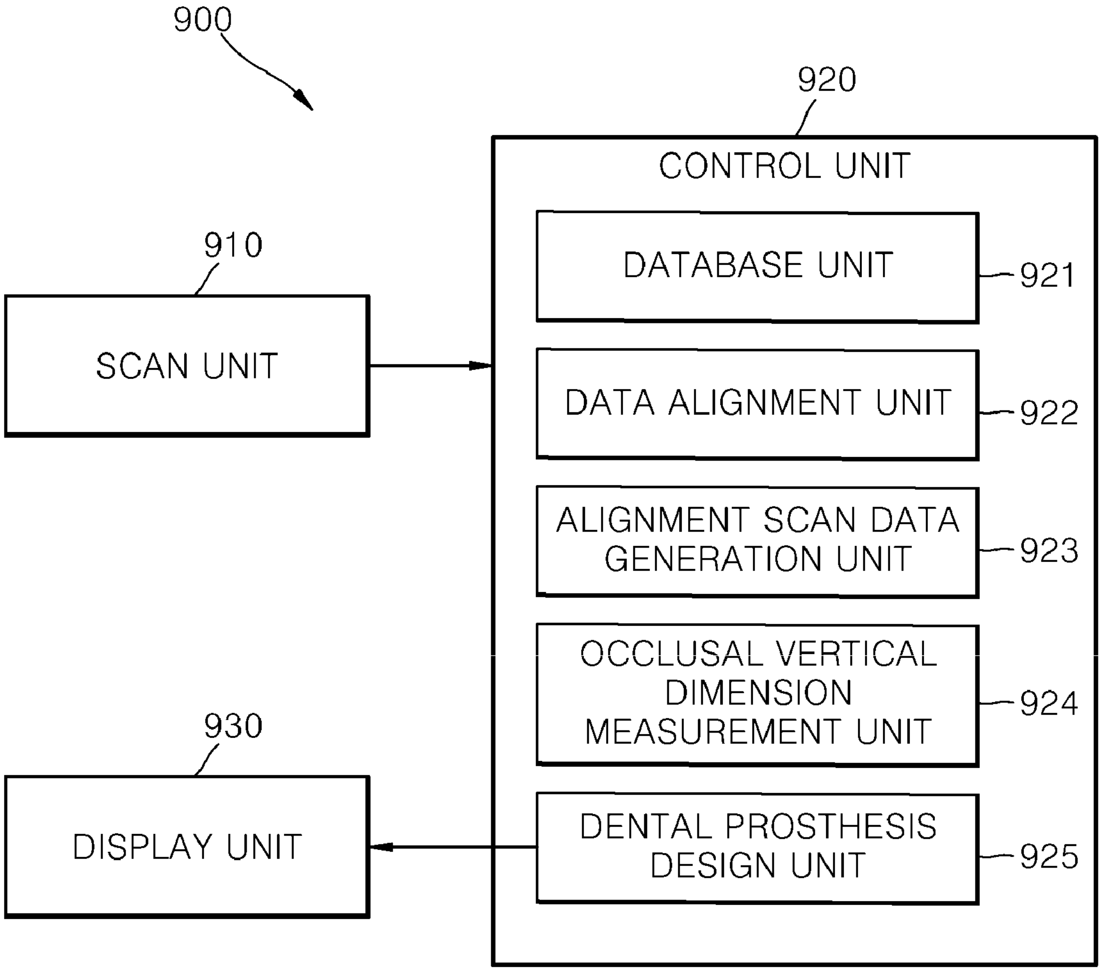
FIG. 18 shows a schematic configuration diagram of a data processing apparatus in which a data processing method according to the present disclosure is performed.

FIG. 18 shows a schematic configuration diagram of a data processing apparatus 900 in which a data processing method according to the present disclosure is performed.

Referring to FIG. 18, the data processing apparatus in which a data processing method according to the present disclosure is performed may include a scan unit 910, a control unit 920, and a display unit 930.

The scan unit 910 may be a device for 3D scanning an object. By way of example, the scan unit 910 may be a handheld 3D scanner which obtains continuous image shots at free scan angles and scan distances with respect to an object. As another example, the scan unit 910 may be a table-type 3D scanner which scans an object by placing the object on a provided tray and rotating or tilting the object. The scan unit 910 may radiate predetermined light such as structured light toward the surface of the object in order to obtain a 3D shape of the object. For example, the scan unit 910 may radiate structured light toward the surface of the object using a built-in light projector, and the light reflected from the surface of the object may be received by a camera of the scan unit 910. The scan unit 910 may obtain scan data of the object through the reflected light received by the camera. The scan data may include a shape of upper and lower jaw data representing the oral cavity shape of the object.

A user may obtain at least one set of upper and lower jaw data and a plurality of sets of occlusion data by using the scan unit 910. In this case, the upper and lower jaw data may be obtained by scanning the pre-medical procedure object or by scanning the post-medical procedure object. Similarly, the occlusion data may also be obtained by scanning the pre-medical procedure object or by scanning the post-medical procedure object. The scan unit 910 may transmit scan data obtained by scanning the object to a control unit 920 described later.

The control unit 920 may store the scan data obtained by the scan unit 910, generate the alignment scan data by aligning the upper and lower jaw data and the occlusion data among the scan data, measure the occlusal vertical dimension of the generated alignment scan data, and enable the user to design a dental prosthesis based on the alignment scan data.

By way of example, the control unit 920 may include a database unit 921. The database unit 921 may store the scan data obtained by the scan unit 910 scanning the object. The database unit 921 may be at least one of known storage devices including, but not limited to, a hard disk drive, a solid state drive, and a flash drive. The database unit 921 may be a physical storage device or may be a cloud storage. The database unit 921 may include a logic for aligning the scan data, a logic for generating the alignment scan data, a logic for measuring an occlusal vertical dimension, a logic for designing a dental prosthesis, a logic for controlling the scan unit 910, and a logic for controlling the display unit 930.

The control unit 920 may include a data alignment unit 922. The data alignment unit 922 may align the upper and lower jaw data and the occlusion data. For example, the data alignment unit 922 may align the pre-medical procedure occlusion data and the pre-medical procedure upper and lower jaw data, and may align the pre-medical procedure occlusion data and the post-medical procedure upper and lower jaw data. Also, the data alignment unit 922 may align the post-medical procedure occlusion data and the pre-medical procedure upper and lower jaw data, and may align the post-medical procedure occlusion data and the post-medical procedure upper and lower jaw data. In addition, since the upper and lower jaw data includes the upper jaw data and the lower jaw data, the upper jaw data may include the pre-medical procedure upper jaw data and the post-medical procedure upper jaw data, and the lower jaw data may include the pre-medical procedure lower jaw data and the post-medical procedure lower jaw data. As described above, the data alignment unit 922 may align the occlusion data and the upper and lower jaw data before and after the medical procedure, and a known alignment logic may be used as an alignment scheme of the occlusion data and the upper and lower jaw data. As described above, the term 'medical procedure' may refer to a specific treatment applied to an object, including tooth preparation.

Also, the control unit 920 may include an alignment scan data generation unit 923. The alignment scan data generation unit 923 may generate the alignment scan data based on the upper and lower jaw data and the occlusion data aligned by the data alignment unit 922. By way of example, the alignment scan data generation unit 923 may generate the first alignment scan data obtained by aligning the upper and lower jaw data obtained by scanning the post-medical procedure object with the first occlusion data obtained by scanning the buccal surface of the pre-medical procedure object. In another example, the alignment scan data generation unit 923 may generate the second alignment scan data obtained by aligning the upper and lower jaw data obtained by scanning the post-medical procedure object with the second occlusion data obtained by scanning the buccal surface of the post-medical procedure object. In this way, the alignment scan data generation unit 923 may generate a plurality of sets of alignment scan data, and at least some or all of the plurality of sets of alignment scan data may be displayed on a user interface screen displayed on the display unit 930 to be described later. There is an advantage of being able to allow the user to design an optimal dental prosthesis for the patient based on a plurality of sets of alignment scan data generated by the alignment scan data generating unit 923.

In addition, the control unit 920 may include an occlusal vertical dimension measurement unit 924. The occlusal vertical dimension measurement unit 924 may measure the occlusal vertical dimension of each of the plurality of sets of alignment scan data generated by the alignment scan data generation unit 923. The occlusal vertical dimension may be a distance between oral cavity vestibules of the upper and lower jaw data, and the occlusal vertical dimension may be measured based on at least one of location information and curve information of the upper and lower jaw data. The occlusal vertical dimension measurement unit 924 may compare the occlusal vertical dimensions which the plurality of sets of alignment scan data have respectively. The alignment scan data having the largest occlusal vertical dimension measured by the occlusal vertical dimension measurement unit 924 may be determined as the alignment scan data that is a basis for designing a dental prosthesis. The process of measuring the occlusal vertical dimension is the same as the above description, and thus a detailed description thereof will be omitted.

Additionally, the control unit 920 may include a dental prosthesis design unit 925. The dental prosthesis design unit 925 may design a dental prosthesis using the alignment scan data, which is the basis of dental prosthesis design, determined by the alignment scan data generation unit 923 and the occlusal vertical dimension measurement unit 924. However, in addition to the alignment scan data having the maximum occlusal vertical dimension in the occlusal vertical dimension measurement unit 924, the various plurality of sets of alignment scan data for precisely designing the outer surface (contact surface with adjacent tooth or antagonist tooth) and inner surface (contact surface with preparation tooth) of the dental prosthesis may be used.

The display unit 930 may visually display at least some of the processes performed by the scan unit 910 and the control unit 920, including a process of obtaining scan data in real time by the scan unit 910, a process of aligning data to generate alignment scan data, a process of measuring an occlusal vertical dimension, and a process of designing a dental prosthesis. The display unit 930 may be at least one of a monitor, a tablet PC, and known visual display devices including a touch screen. The user may visually and easily check a plurality of sets of alignment scan data through a user interface screen displayed on the display unit 930. In addition, since the user can easily check the occlusal vertical dimensions measured by the occlusal vertical dimension measurement unit 924 as well as the shape of each of the plurality of sets of alignment scan data, a digital model of the alignment scan data most suitable for designing a dental prosthesis can be selected and used as a reference for dental prosthesis design.

The above description is merely illustrative of the technical idea of the present disclosure, and various modifications and changes can be made by those of ordinary skill in the art to which the present disclosure pertains, without departing from the essential characteristics of the present disclosure.

Accordingly, the embodiments disclosed in the present disclosure are not for limiting, but for explaining the technical spirit of the present disclosure, and the scope of the technical spirit of the present disclosure is not limited by these embodiments. The protection scope of the present disclosure should be construed based on the following claims, and all technical ideas within the scope equivalent thereto should be construed as being included in the scope of the present disclosure.

INDUSTRIAL APPLICABILITY

An object of the present disclosure is to provide a data processing method for providing optimal treatment to a patient by obtaining a plurality of sets of alignment scan data from obtained scan data and by comparing the plurality of sets of alignment scan data.

The invention claimed is:

1. A data processing method comprising:

obtaining scan data including at least one set of upper and lower jaw data and a plurality of sets of occlusion data by scanning an object;

obtaining a plurality of sets of alignment scan data by aligning the upper and lower jaw data to each of different sets of occlusion data among the plurality of sets of occlusion data; and comparing the plurality of sets of alignment scan data, wherein the upper and lower jaw data include pre-procedure upper and lower jaw data obtained by scanning the object before a procedure and post-procedure upper and lower jaw data obtained by scanning the object after the procedure, wherein the plurality of sets of occlusion data includes first occlusion data obtained by scanning the object before the procedure and second occlusion data obtained by scanning the object after the procedure, and wherein the plurality of sets of alignment scan data are generated by combination of the upper and lower jaw data and the plurality of sets of occlusion data.

2. The data processing method of claim 1, wherein the plurality of sets of alignment scan data includes first alignment scan data obtained by aligning upper and lower jaw data obtained by scanning the post-medical procedure object to the first occlusion data, and second alignment scan data obtained by aligning upper and lower jaw data obtained by scanning the post-medical procedure object to the second occlusion data.

3. The data processing method of claim 2, wherein the plurality of sets of alignment scan data includes third alignment scan data obtained by aligning upper and lower jaw data obtained by scanning the pre-medical procedure object to the first occlusion data, and fourth alignment scan data obtained by aligning upper and lower jaw data obtained by scanning the pre-medical procedure object to the second occlusion data.

4. The data processing method of claim 2, further comprising designing a dental prosthesis based on the first alignment scan data.

5. The data processing method of claim 1, further comprising measuring occlusal vertical dimensions of the plurality of sets of alignment scan data.

6. The data processing method of claim 5, wherein the occlusal vertical dimension is a distance between oral cavity vestibules of the upper and lower jaw data.

7. The data processing method of claim 5, wherein the occlusal vertical dimension is measured based on at least one of location information and curve information of the upper and lower jaw data.

8. The data processing method of claim 1, wherein the comparing of the plurality of sets of alignment scan data includes comparing occlusal vertical dimensions which the plurality of sets of alignment scan data have respectively.

9. The data processing method of claim 1, further comprising displaying the plurality of sets of alignment scan data and occlusal vertical dimensions of the plurality of sets of alignment scan data.

* * * * *